(12) United States Patent
Chapuis

(10) Patent No.: US 8,012,462 B2
(45) Date of Patent: Sep. 6, 2011

(54) 1-OXASPIRO (4, 5) DEC-3-ENE DERIVATIVES AS PERFUMING INGREDIENTS

(75) Inventor: Christian Chapuis, Mies (CH)

(73) Assignee: Firmenich SA, Geneva (CH)

( * ) Notice: Subject to any disclaimer, the term of this patent is extended or adjusted under 35 U.S.C. 154(b) by 456 days.

(21) Appl. No.: 12/294,591

(22) PCT Filed: Apr. 17, 2007

(86) PCT No.: PCT/IB2007/051369
§ 371 (c)(1),
(2), (4) Date: Sep. 25, 2008

(87) PCT Pub. No.: WO2007/129236
PCT Pub. Date: Nov. 15, 2007

(65) Prior Publication Data
US 2009/0104140 A1    Apr. 23, 2009

(30) Foreign Application Priority Data
May 4, 2006    (WO) .................. PCT/IB2006/051410

(51) Int. Cl.
*C07D 307/94*    (2006.01)
*A61K 8/49*    (2006.01)
*C11D 3/50*    (2006.01)
*A61L 9/01*    (2006.01)

(52) U.S. Cl. ........... 424/76.1; 510/103; 512/9; 514/772; 549/331

(58) Field of Classification Search ...................... None
See application file for complete search history.

(56) References Cited

U.S. PATENT DOCUMENTS

| 4,179,448 A | 12/1979 | Schulte-Elte et al. ... 260/346.11 |
| 4,336,197 A | 6/1982 | Fankhauser .................... 549/331 |
| 4,465,618 A | 8/1984 | Fankhauser ............... 252/522 R |

FOREIGN PATENT DOCUMENTS

| CH | 599 758 | 5/1978 |
| DE | 263 4077 | 2/1977 |
| EP | 33 959 | 8/1981 |

OTHER PUBLICATIONS

Ehrenfreund et al, caplus an 1974:552446.*
International Search Report PCT/IB2007/051369 Dated Oct. 2, 2007 and Written Opinion.

* cited by examiner

*Primary Examiner* — Sun Jae Loewe
(74) *Attorney, Agent, or Firm* — Winston & Strawn LLP

(57) ABSTRACT

The present invention relates to a spiroheterocycle derivative which is a useful perfuming ingredient. Furthermore, the present invention concerns also the compositions or articles containing this compound.

9 Claims, No Drawings

1-OXASPIRO (4, 5) DEC-3-ENE DERIVATIVES AS PERFUMING INGREDIENTS

This application is a 371 filing of International Patent Application PCT/IB2007/051369 filed Apr. 17, 2007.

TECHNICAL FIELD

The present invention relates to the field of perfumery. More particularly, it concerns a compound of formula (I), as defined below, and its uses in perfumery. The present invention concerns also the compositions or articles containing said compound.

PRIOR ART

To the best of our knowledge, none of the invention's compounds is known.

DESCRIPTION OF THE INVENTION

We have now surprisingly discovered that a compound of formula

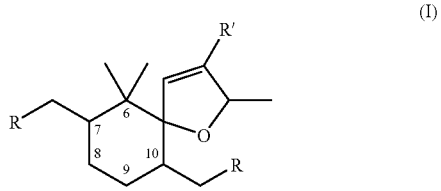

(I)

wherein each R and R' represents, independently of simultaneously, a hydrogen atom or a methyl group, and in the form of any one of its stereoisomes or a mixture thereof; can be used as perfuming ingredient, for instance to impart odor notes of the aromatic type.

According to an embodiment of the invention, the compounds of formula (I) wherein the R' group is a hydrogen atom is particularly appreciated.

According to an embodiment of the invention, the compounds of formula (I) wherein the R groups are hydrogen atoms are particularly appreciated.

According to another embodiment of the invention, the compounds of formula (I) wherein the two substituents in positions 7 and 10 are in a relative configuration trans, are particularly appreciated.

As example of the present invention one may cite (7RS, 10RS)-2,6,6,7,10-pentamethyl-1-oxaspiro[4,5]dec-3-ene, which has an odor characterized by an aromatic note of the laurel-marjoram type as well as a fruity note of the prune, cassis juice type. Eucalyptus, damascony and sulfury notes are also present, providing thus to this compound a quite complex and elegant olfactive profile.

In the prior art there is known a few close structural analogues which have an interesting odor, namely Eta or Isospirene (disclosed respectively into EP 33959 and U.S. Pat. No. 4,179,448) or also 2,6,9,10,10-pentamethyl-1-oxaspiro[4,5]deca-3,6-diene (described also in EP 33959 or in CH 599758).

When the odor of the invention's compounds is compared to the one of Eta or Isospirene, then it distinguishes itself by having an aromatic note, as well as by having an eucalyptus and sulfury notes, the latter being just a vague nuance or not perceivable in the prior art compounds.

When the odor of the invention's compounds is compared to the one of 2,6,9,10,10-pentamethyl-1-oxaspiro[4,5]deca-3,6-diene, then it distinguishes itself again by having an aromatic note, as well as by having an eucalyptus note, the latter being just a faint nuance in the prior art compounds. Furthermore, the invention's compound distinguishes itself from said prior art compound by lacking, or by not possessing significant, minty and/or grapefruit notes which are characteristic of the prior art compound. Said differences lend the invention's compounds and the prior art compounds to be each suitable for different uses, i.e. to impart different organoleptic impressions.

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing compound (I) and which can be advantageously employed in perfumery industry as active ingredients.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs-und Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, by using techniques such as spray-drying, agglomeration or yet extrusion; or consists of a coating encapsulation, including coacervation and complex coacervation techniques.

Generally speaking, by "perfumery base" we mean here a composition comprising at least one perfuming co-ingredient.

Said perfuming co-ingredient is not of the formula (I). Moreover, by "perfuming co-ingredient" it is meant here a compound which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:
i) as perfuming ingredient, at least one compound of formula (I), as defined above, or an invention's perfuming composition; and
ii) a consumer product base;
is also an object of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 5% by weight, or even more, of the compounds of the invention based on the weight of the composition into which they are incorporated. Concentrations lower than these, such as in the order of 0.1% to 3% by weight, can be used when these compounds are incorporated into perfumed articles, percentage being relative to the weight of the article.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacements δ are indicated in ppm with respect to TMS as standard, the coupling constants J are expressed in Hz.

Example 1

Preparation of the Invention Compound

A) Synthesis of a Mixture of 1-(3-hydroxy-1-butynyl)-2,2,c-3,t-6-tetramethyl-R-1-cyclohexanol and 1-(3-hydroxy-1-butynyl)-2,2,t-3,c-6-tetramethyl-R-1-cyclohexanol To a mixture of 52.2 g (0.78 mol) 3-butyn-2-ol in 600 mL diethyl ether was added a solution of ethylmagnesium bromide (3M in $Et_2O$) over 90 min. An exothermic reaction and gas evolution was observed during addition. After stirring 1 h at room temperature 120 g (0.78 mol) of trans-2,2,3,6-tetramethyl-1-cyclohexanone in 120 mL diethyl ether were added over 50 min. The mixture was stirred for 2 days at room temperature and poured onto 300 g ice in small portions. After addition of 800 mL of a saturated aqueous NH$_4$Cl solution and extraction with 2×500 mL diethyl ether the combined organic phases were washed three times with 200 mL H$_2$O, dried over Na$_2$SO$_4$ and concentrated under vacuum. Distillation (b.p. 99° C./0.051 mbar) afforded 118.4 g (67%) of the diol as mixture of 4 diastereomers.

$^1$H-NMR (deduced from the mixture): 0.81-1.13 (m, 12H), 1.20-2.43 (m, 11H), 4.53-4.61 (m, 1H).

$^{13}$C-NMR (selected main signals from mixture): 13.6, 16.2, 16.5, 16.7, 16.8, 17.0, 17.4, 17.5, 17.2, 22.9, 23.5, 23.6, 24.5, 24.6, 24.6, 24.7, 27.3, 28.1, 29.0, 29.9, 30.0, 31.9, 34.0, 35.9, 36.0, 36.5, 36.6, 36.9, 36.9, 38.2, 38.3, 40.4, 41.4, 42.2, 58.3, 77.2, 77.6, 79.0, 84.3, 86.6, 86.6, 86.7, 86.8, 87.2, 87.2, 87.3, 87.3, 89.4.

MS (main stereoisomer): 224 (1.3, M+), 206 (1.9), 191 (39), 188 (6), 173 (13), 163 (26), 149 (16), 135 (27), 121 (61), 111 (47), 96 (54), 93 (40), 83 (28), 80 (27), 77 (38), 69 (41), 55 (66), 43 (100), 41 (83).

B) Synthesis of 1-[(1Z)-3-hydroxy-1-butenyl]-2,2,R-3,T-6-tetramethylcyclohexanol A solution of 118.4 g (0.52 mol) of the product obtained under A) above in 600 mL EtOH was hydrogenated at normal pressure in the presence of 2.34 g Pd on CaCO$_3$ (5%) as a catalyst. After 24 h the mixture was filtered through Celite® and the solvent was evaporated. Distillation (b.p. 103° C./0.093 mbar) afforded 112.0 g (95%) yield of a colourless oil as a mixture of 4 diastereomers.

$^1$H-NMR (deduced from the mixture): 0.81-1.03 (m, 12H), 1.19-1.94 (m, 9H), 3.05 (br, 2H), 4.77-4.92 (m, 1H), 5.25-5.63 (m, 2H).

$^{13}$C-NMR (selected main signals from mixture): 14.2, 16.4, 16.5, 16.5, 16.6, 16.6, 16.7, 16.7, 17.5, 22.7, 23.2, 23.7, 23.8, 29.6, 29.8, 30.2, 30.3, 30.3, 31.5, 31.7, 34.7, 35.0, 35.2, 35.4, 37.8, 37.9, 42.2, 42.4, 64.1, 64.1, 64.4, 82.1, 82.4, 130.4, 130.7, 134.3, 134.6, 134.7, 135.8, 136.5.

MS (main stereoisomer): 226 (0.7, M+), 208 (27), 192 (3), 175 (3), 165 (9), 141 (6), 137 (9), 135 (6), 123 (100), 111 (41), 109 (45), 95 (44), 82 (46), 69 (27), 55 (46), 43 (44), 41 (31).

C) Preparation of (7RS,10RS)-2,6,6,7,10-pentamethyl-1-oxaspiro[4,5]dec-3-ene A solution of 1-[(1Z)-3-hydroxy-1-butenyl]-2,2,R-3,T-6-tetramethylcyclohexanol (1.00 g, 4.4 mmol) in DMSO (10 ml) under N$_2$ was heated at reflux for 18 hours. The cold reaction mixture was diluted with H$_2$O (20 ml) and extracted with Et$_2$O (3×20 ml). The organic phase was washed with H$_2$O, dried (Na$_2$SO$_4$), concentrated and purified by bulb-to-bulb distillation to afford a 29:21:19:17 mixture of diastereoisomers in 73% yield. Bp: 100/0.27 mbar.

$^1$H-NMR deduced from the mixture: 0.7-0.9 (2s+2d, J=7, 12H); 1.2-1.3 (d, J=7, 3H); 1.0-2.0 (m, 6H); 4.87 (m, 1H); 5.5-5.8 (m, 2H).

$^{13}$C-NMR selected main signals from the mixture: 16.2; 16.3; 16.8; 17.7; 22.3; 24.4; 30.7; 32.9; 36.3; 39.7; 82.4; 83.0; 130.4; 131.3

Example 2

Preparation of a Perfuming Composition

A perfuming base was prepared by admixing the following ingredients:

| Ingredient | Parts by weight |
| --- | --- |
| 10%* Amyl acetate | 10 |
| Benzyl acetate | 15 |
| Cyclanol acetate | 10 |
| Terpenyl acetate | 50 |
| Hexyl acetate | 10 |
| Hexylcinnamic aldehyde | 150 |
| Gamma undecalactone | 10 |
| 4-Nonanolide | 10 |
| Cetalox ®[1] 10% APV | 10 |
| 1%* Cis-3-Hexenol | 100 |
| Citronellol | 20 |
| 4-Cyclohexyl-2-methyl-2-butanol | 50 |
| 10%* Damascone Alpha | 25 |
| 10%* Dorinone ®[2] Beta | 20 |
| Eugenol | 15 |
| Farenal ®[3] | 5 |
| 10%* 2-Methyl-4-(2,2,3-trimethyl-3-cyclopenten-1-yl)-4-penten-1-ol | 10 |
| Geraniol Brut | 140 |
| Habanolide ®[4] | 40 |
| Hédione ®[5] | 150 |
| 10%* Indomethylene | 10 |
| Iso E Super ®[6] | 65 |
| 10%* Labdanum | 5 |
| Lilial ®[7] | 15 |
| Linalol | 150 |
| Lorysia ®[8] | 60 |
| 10%* Muscenone Delta | 10 |
| 1%* (+−)-(E)-4-(2,2,C-3,t-6-Tetramethyl-r-1-cyclohexyl)-3-buten-2-one | 70 |
| 10%* Rose Oxide | 30 |
| Phenethylol | 20 |
| Romascone ®[9] | 5 |
| Hexyl salicylate | 30 |
| Terpene Orange | 50 |
| Terpineol | 40 |
| Thuyac[10] | 25 |
| 2,2,5-Trimethyl-5-pentyl-1-cyclopentanone | 10 |
| Verdox ®[11] | 100 |
| Beta Ionone | 5 |
| 2,4-Dimethyl-3-cyclohexene-1-carbaldehyde | 10 |
| | 1560 |

*in dipropyleneglycol
[1] Dodecahydro-3a,6,6,9a-tetramethyl-naphtho[2,1-b]furan; origin: Firmenich SA, Switzerland
[2] 1-(2,6,6-Trimethyl-1-cyclohexen-1-yl)-2-buten-1-one; origin: Firmenich SA, Switzerland
[3] 2,6,10-Trimethyl-9-undecenal origin: Symrise AG, Germany
[4] Pentadecenolide; origin: Firmenich SA, Switzerland
[5] Methyl dihydrojasmonate; origin: Firmenich SA, Switzerland
[6] 1-(Octahydro-2,3,8,8-tetramethyl-2-naphtalenyl)-1-ethanone; origin: International Flavors & Fragrances, USA
[7] 3-(4-Tert-butylphenyl)-2-methylpropanal; origin: Givaudan-Roure SA, Vernier, Switzerland
[8] 4-(1,1-Dimethylethyl)-1-cyclohexyl acetate; origin: Firmenich SA, Switzerland
[9] Methyl 2,2-dimethyl-6-methylene-1-cyclohexanecarboxylate; origin: Firmenich SA, Switzerland
[10] Mixture of 1-(3,3-dimethyl-1-cyclohexyl)-1-ethanone and 2,6,6-trimethyl-1-cycloheptanone; origin: Firmenich SA, Switzerland
[11] 2-Tert-butyl-1-cyclohexyl acetate; origin: IFF, USA The addition of 40 parts by weight of (7RS,10RS)-2,6,6,7,10-pentamethyl-1-oxaspiro[4,5]dec-3-ene to the above described perfume provided the latter an aromatic (laurel), eucalyptus note, slightly Buchu, a bit sulfury (of the kind of 8-mercapto-3-p-menthanone) quite unique. The addition of the same amount of Eta or Isospirene rather imparted a bourgeon-cassis note, and not at all aromatic notes.

Example 3

Preparation of a Perfuming Composition

A perfuming base was prepared by admixing the following ingredients:

| Ingredient | Parts by weight |
| --- | --- |
| Hexylcinnamic aldehyde | 150 |
| 10%* Corps Praline | 80 |
| Geraniol | 85 |
| Habanolide ®[1)] | 100 |
| Hedione ®[2)] | 100 |
| 10%* Crystal Moss | 50 |
| (1'R)-2-[2-(4'-Methyl-3'-cyclohexen-1'-yl)propyl]cyclopentanone | 25 |
| 10%* Neobutenone ®[3)] | 25 |
| Cis-2-methyl-4-propyl-1,3-oxathiane | 25 |
| 10%* Rose Oxide | 30 |
| Pinene | 250 |
| 10%* 2-Methyl-3-hexanone oxime | 10 |
| Vetyver | 25 |
| 2,4-Dimethyl-3-cyclohexene-1-carbaldehyde | 25 |
| | 980 |

*in dipropyleneglycol
[1)]Pentadecenolide; origin: Firmenich SA, Switzerland
[2)]Methyl dihydrojasmonate; origin: Firmenich SA, Switzerland
[3)]1-(5,5-Dimethyl-1-cyclohexen-1-yl)-4-penten-1-one; origin: Firmenich SA, Switzerland The addition of 20 parts by weight of (7RS,10RS)-2,6,6,7,10-pentamethyl-1-oxaspiro[4,5]dec-3-ene to the above-described perfume provided a nice Buchu-Laurel note and et transformed this perfume into an elegant laurel leave tonality. Again, the addition of the same amount of Eta or Isospirene rather imparted a bourgeon-cassis note, and not at all aromatic notes.

The invention claimed is:
1. A compound of formula

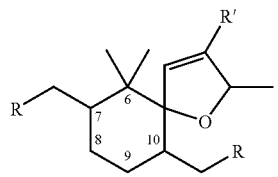

wherein each R and R' represents a hydrogen atom or a methyl group, or the compound is a stereoisomer or mixture of stereoisomers thereof.

2. A compound according to claim 1, specifically as (7RS, 10RS)-2,6,6,7,10-pentamethyl-1-oxaspiro[4,5]dec-3-ene.

3. A method to confer, enhance, improve or modify the odor properties of a perfuming composition or of a perfumed article, which method comprises adding to said composition or article an effective amount of at least a compound of formula (I), as defined in claim 1, as a perfuming ingredient.

4. The method according to claim 3, wherein the compound is (7RS,10RS)-2,6,6,7,10-pentamethyl-1-oxaspiro[4,5]dec-3-ene.

5. A perfuming composition comprising:
   i) as perfuming ingredient, at least one compound as defined in claim 1;
   ii) at least one ingredient selected from the group consisting of a perfumery carrier and a perfumery base; and
   iii) optionally at least one perfumery adjuvant.

6. The composition according to claim 5, wherein the compound is (7RS,10RS)-2,6,6,7,10-pentamethyl-1-oxaspiro[4,5]dec-3-ene.

7. A perfumed article comprising:
   i) as perfuming ingredient, at least one compound of formula (I) as defined in claim 1; and
   ii) a consumer product base.

8. A perfumed article according to claim 7, wherein the compound is (7RS,10RS)-2,6,6,7,10-pentamethyl-1-oxaspiro[4,5]dec-3-ene.

9. A perfumed article according to claim 7, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

* * * * *